United States Patent [19]

Wharff et al.

[11] Patent Number: 4,938,744
[45] Date of Patent: Jul. 3, 1990

[54] NEEDLE ASSEMBLY

[75] Inventors: Prentice C. Wharff, Walnut Creek; Renato R. Salumbides, San Dimas, both of Calif.

[73] Assignee: Miles Laboratories, Inc., Elkhart, Ind.

[21] Appl. No.: 699,714

[22] Filed: Feb. 8, 1985

[51] Int. Cl.$^5$ .............................................. A61M 5/32
[52] U.S. Cl. ...................................... 604/263; 604/199
[58] Field of Search ............... 604/263, 272, 192, 197, 604/199

[56] References Cited

U.S. PATENT DOCUMENTS

| | | | |
|---|---|---|---|
| 3,523,530 | 8/1970 | Pagrones | 604/263 |
| 4,091,811 | 5/1978 | Bates et al. | 128/214.4 |
| 4,205,767 | 6/1980 | Shackelford | 604/263 |
| 4,508,534 | 4/1985 | Garver, Sr. et al. | 604/263 |
| 4,530,697 | 6/1985 | Kjhlemann et al. | 604/263 |

*Primary Examiner*—Stephen C. Pellegrino
*Attorney, Agent, or Firm*—James A. Giblin; Pamela A. Simonton

[57] ABSTRACT

Double-protected needle assembly comprising a needle-handle portion and a needle-protecting portion. The needle-handle portion includes a bevel-tipped needle attached to and extending from it into the needle-protector portion. The needle protecting portion comprises a rigid, tamper proof member completely enclosing the needle and attached to the needle-handle portion at a resilient tear seal member adapted to break when a twisting force is applied to either the handle portion or the protecting member. The tear seal is adapted to remove liquid from the surface of the needle when the protector is withdrawn to expose the needle. Within the protector, but not attached thereto, is a relatively soft inner tubular enclosure completely enclosing the needle extending beyond its bevel tip and adapted to prevent contact of the bevel tip with any portion of the rigid protector during assembly or when the protector is removed. The inner tubular enclosure is retained loosely within the protector by the tear seal member which is bonded to the rigid protector during steam sterilization.

4 Claims, 1 Drawing Sheet

U.S. Patent  Jul. 3, 1990  4,938,744
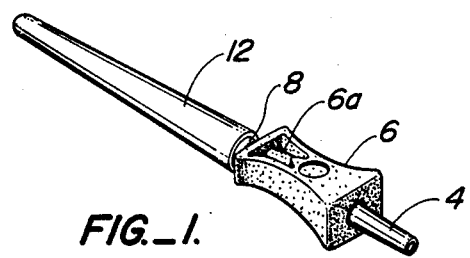
FIG._1.
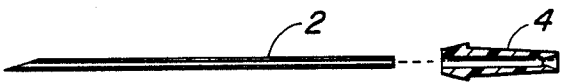
FIG._2.
FIG._3.
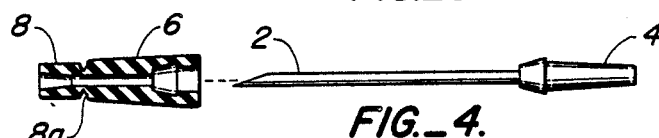
FIG._4.
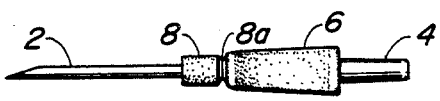
FIG._5.
FIG._6.
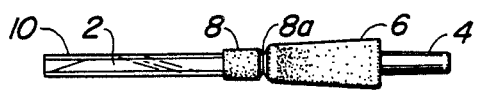
FIG._7.
FIG._8.
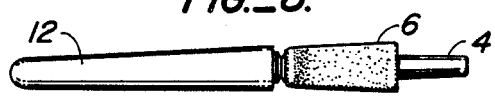
FIG._9.
FIG._10.

NEEDLE ASSEMBLY

BACKGROUND OF THE INVENTION

1. Field:

This disclosure is concerned generally with medically useful needle assemblies and is especially concerned with a venipuncture needle assembly used in conjunction with blood collection equipment.

2. Prior Art:

Various needle assemblies consisting of sterile hypodermic or venipuncture needles enclosed in needle protectors are well known and the subject of many patents. One such recent patent is described in U.S. Pat. No. 4,435,177, the teachings of which are incorporated herein by reference to it.

Very generally, the needle protector portion of medically useful needle assemblies are of at least two types. In one type, the bevel tip of a needle is embedded in a relatively soft material such as rubber or cork stopper as shown in U.S. Pat. Nos. 2,688,963; 2,667,163; 2,688,964; and 3,416,657. As pointed out in U.S. Pat. No. 4,435,177, there are known disadvantages to this type of protector. In another type of needle protector, the needle is enclosed in a relatively rigid (hard) plastic material. A needle of this type is shown in U.S. Pat. No. 4,435,177 and in many of the other patents cited therein. Although the more rigid needle protectors are intended to protect the needle (especially its fine-edged bevel tip) after final assembly and, to a certain extent during storage, the hard protectors often damage the bevel tip of the needle during assembly steps or after or while the protector is removed. Even a slight contact of the very sharp bevel edge of the needle against a hard protector can cause damage to the needle tip. This damage may cause unnecessary pain and trauma to a patient. This is especially true for venipuncture needle assemblies where relatively large gauge needles are used.

As can be appreciated, the final choice of a relatively hard vs. a relatively soft needle protector typically involves a trade off of benefits and detriments depending on the intended use of the needle assembly. It has now been found that the respective advantages of both hard and soft needle protectors can be obtained in a single needle assembly which is relatively easy and inexpensive to manufacture. Details of our discovery are described below.

SUMMARY OF THE INVENTION

Our needle assembly comprises a needle-handle portion and a needle protector portion connected to each other at a resilient tear seal member having a circumferential scored portion adapted to break when either the protector or needle-handle (or both) is (are) twisted relative to one another. A portion of the tear seal is adapted to remain in the protector as it is withdrawn from the needle to remove any liquid remaining on the needle surface, thus acting as a wiper. Such liquid often is present on a needle due to the presence of anticoagulant solution forced through the needle tip during heat sterilization or handling. If not removed prior to venipuncture, the liquid may cause an unnecessary stinging sensation. Enclosed within the relatively rigid needle protector, and essential to the present invention, is a relatively soft, inner tubular member fully enclosing the needle and extending beyond its bevel tip and protecting it from contact with the outer rigid protector. The inner tubular member is unattached to the outer rigid protector but retained within it by that portion of the resilient tear seal (the needle wiper) which remains with the needle protector as it is withdrawn from the needle. In preferred embodiments, the relatively soft inner tubular member is a piece of clear polyvinyl chloride tubing having an inner diameter adapted to easily receive the needle (i.e. the inner diameter of the tubing is at least as large as the outer diameter of the needle). In a further preferred embodiment, the needle assembly is attached to and part of a blood bag system including a blood collection bag.

BRIEF DESCRIPTION OF THE FIGURES

FIG. 1 is a perspective view of the needle assembly of this disclosure.

FIGS. 2–8 show the various components of the needle assembly in the sequence in which they are assembled.

FIG. 9 shows the final needle assembly and FIG. 10 is a perspective view of the assembly of FIG. 1 but after the needle protector has been removed.

SPECIFIC EMBODIMENTS

The invention of this disclosure is illustrated in the Figures. The term relatively hard refers to a degree of hardness (of the rigid outer protector) sufficient to damage the bevel tip of the needle if contacted with the protector. Relatively soft refers to a degree of hardness (of the inner tubing) insufficient to cause such damage on contact. Resilient refers to that degree of flexibility sufficient to support a liquid wiping action against a hard surface.

FIG. 1 is a perspective view of the completed assembly showing a portion of the needle-retainer 4 extending from the needle handle 6, having a bevel indicator 6a, which is a simple depression indicating the alignment (or orientation) of the bevel tip of the needle, not seen in FIG. 1. Connected to the needle handle 6 is the outer, rigid and relatively hard needle protector 12 which, like needle-retainer 4, may be made from a conventional medical grade rigid polycarbonate plastic. Connected by conventional heat weld to retainer 4 is conventional PVC tubing 14 (see FIG. 10). The actual assembly sequences, an important aspect of this disclosure, are illustrated in FIGS. 2–9.

FIG. 2 shows the needle 2 (e.g. stainless steel 16 gauge for venipuncture) having a bevel-tip before its insertion and bonding within tubular needle retainer 4, a polycarbonate plastic tube to which the steel needle is bonded via a cyanoacrylate bond.

FIG. 3 shows the needle 2 bonded within the retainer 4.

FIG. 4 shows the assembly of FIG. 2 prior to its insertion into the needle handle 6, a resilient yet firm PVC compound (PVC compounded with calcium carbonate using conventional forming techniques) having a wiper portion 8 connected to it at tear seal 8a, a circumferentially scored portion about 27-mils thick adapted to break when 8 and 6 are twisted relative to each other. Retainer portion 4 is bonded to the inner portions of the needle handle 6 using a heat weld bond.

FIG. 5 shows the needle retainer 4 with attached needle 2 fully inserted into and bonded within needle handle 6.

FIG. 6 shows the relatively soft inner needle protector 10 prior to insertion over the needle 2 of the assembly of FIG. 5.

FIG. 7 shows the inner needle protector 10 (preferably transparent PVC tubing) inserted on the needle 2.

FIG. 8 shows the relatively hard rigid needle protector prior to insertion over the protected needle portion of FIG. 7. It should be noted that the inner diameter of outer protector 12 is large enough to easily accept both the needle 2 and inner protector 10 (in place on the needle) but, at least at its orifice, small enough in diameter to engage resilient portion 8 in a firm friction fit. When the final assembly (see FIG. 1) is sterilized (e.g. 114½° C. for 50 minutes), the resilient portion 8 of needle handle 6 becomes bonded via a "heat weld" to the inner diameter of the polycarbonate outer rigid protector 12. The bond force is greater (stronger) than that required to break tear seal 8a when the protector 10 and handle 6 are twisted apart. The consequence is that resilient portion 8 breaks off handle 6 and remains with outer protector 12. Very importantly, the broken off resilient portion 8 has an inner diameter about the same as the outer diameter of the needle 2 and, thus, serves as a wiper of the needle as the protector is withdrawn, thus removing any moisture that may have been forced under the protector via the needle orifice during sterilization and handling.

FIG. 10 illustrates the retained position of resilient portion 8 in outer protector 12 after the protector 12 is removed and the tamper-proof (or tamper-indicating) tear seal 8a has been broken.

As can be appreciated, the needle assembly of this disclosure combines the benefits of a relatively hard rigid outer needle protector (protects against rough handling and shipment, etc.) with the benefits of a relatively soft protector (protects the delicate bevel edge of the needle) in a single assembly that also provides a wiping action on the needle as the outer protector cap is removed. The combined benefits are possible because of the novel sequence of steps disclosed herein and the unattached nature of the inner needle protector once in place in the completed assembly. We are unaware of any needle assembly which uses such an unattached, yet contained, soft inner needle protector to protect the bevel tip of the needle during assembly, shipment and opening.

Given the above disclosure, other variations will occur to those skilled in the art. Accordingly, it is intended that the above-described example should be considered merely illustrative and that the invention disclosed herein should be limited only by the following claims.

We claim:

1. A double-protected needle assembly comprising a needle having a sharpened bevel-tip, the needle attached to a needle handle and completely enclosed by a rigid, relatively hard, outer needle protector attached to the needle handle by a resilient, tear-seal portion adapted to break when a twisting force is applied to the outer protector or needle handle, the outer protector including a resilient member for removing liquid from the outer surface of the needle when the outer protector is withdrawn from the needle, the resilient member comprising a portion of the tear seal portion and located within the outer needle protector, the outer protector also fully enclosing an unattached, relatively soft inner tubular enclosure completely enclosing the bevel tip of the needle and adapted to prevent contact of the bevel tip with any portion of the outer protector.

2. The assembly of claim 1 wherein the inner tubular enclosure is a piece of polyvinyl chloride tubing covering the majority of the needle length and extending beyond the bevel tip.

3. The assembly of claim 2 wherein the inner tubular enclosure is retained within the outer protector by the resilient liquid removing member.

4. The assembly of claim 1 wherein the needle handle is attached to tubing in communication with a blood collection bag.

* * * * *